(12) United States Patent
Morini et al.

(10) Patent No.: US 7,022,640 B2
(45) Date of Patent: Apr. 4, 2006

(54) 1,3-DIETHERS AND COMPONENTS AND CATALYSTS FOR THE POLYMERIZATION OF OLEFINS, CONTAINING SAID DIETHERS

(75) Inventors: Giampiero Morini, Pavia (IT); Enrico Albizzati, Novara (IT); Giulio Balbontin, Ferrara (IT); Giovanni Baruzzi, Ferrara (IT); Antonio Cristofori, Rovigo (IT)

(73) Assignee: Basell Poliolefine Italia s.r.l., Milan (IT)

( * ) Notice: Subject to any disclaimer, the term of this patent is extended or adjusted under 35 U.S.C. 154(b) by 0 days.

(21) Appl. No.: 10/876,576

(22) Filed: Jun. 28, 2004

(65) Prior Publication Data

US 2004/0235645 A1 Nov. 25, 2004

Related U.S. Application Data

(62) Division of application No. 08/603,497, filed on Feb. 20, 1996, now abandoned.

(30) Foreign Application Priority Data

Feb. 21, 1995 (IT) ........................... MI95A000316
Feb. 21, 1995 (IT) ........................... MI95A000317
Feb. 21, 1995 (IT) ........................... MI95A000318

(51) Int. Cl.
  *B01J 31/00* (2006.01)
(52) U.S. Cl. ............... 502/150; 502/103; 502/104; 502/117; 568/579
(58) Field of Classification Search ........... 502/126, 502/150, 103, 104, 117; 568/579
See application file for complete search history.

(56) References Cited

U.S. PATENT DOCUMENTS

| | | | |
|---|---|---|---|
| 4,220,554 A | 9/1980 | Scata et al. | 210/526 |
| 4,522,930 A | 6/1985 | Albizzati et al. | 502/124 |
| 4,978,648 A | 12/1990 | Barbe et al. | 502/127 |
| 5,068,213 A | 11/1991 | Albizzati et al. | 502/126 |
| 5,095,153 A | 3/1992 | Agnes et al. | 568/660 |
| 5,122,492 A | 6/1992 | Albizzati et al. | 502/126 |
| 5,322,528 A * | 6/1994 | Lu-Dai Sung et al. | 44/336 |
| 5,371,299 A | 12/1994 | Borsotti | 568/672 |
| 5,723,400 A | 3/1998 | Morini et al. | 502/126 |
| 6,395,670 B1 * | 5/2002 | Morini et al. | 502/104 |
| 6,451,726 B1 * | 9/2002 | Zambon et al. | 502/152 |
| 6,468,938 B1 * | 10/2002 | Govoni et al. | 502/126 |
| 6,683,017 B1 * | 1/2004 | Gao et al. | 502/126 |
| 6,797,794 B1 * | 9/2004 | Zambon et al. | 526/351 |
| 6,799,568 B1 * | 10/2004 | Zakharov et al. | 526/128 |
| 6,803,428 B1 * | 10/2004 | Saudemont et al. | 526/124.3 |
| 6,818,583 B1 * | 11/2004 | Morini et al. | 502/103 |
| 6,906,154 B1 * | 6/2005 | Fushimi et al. | 526/124.3 |

FOREIGN PATENT DOCUMENTS

| | | |
|---|---|---|
| EP | 0 045 977 | 2/1982 |
| EP | 0 344 755 | 12/1989 |
| EP | 0 361 494 | 4/1990 |
| EP | 452156 | 10/1991 |
| GB | 967585 | 8/1964 |
| JP | 2-242804 | 9/1990 |

* cited by examiner

Primary Examiner—J. A. Lorengo
Assistant Examiner—Jennine Brown

(57) ABSTRACT

Cyclopolyenic 1,3-diethers wherein the carbon atom in position 2 belongs to a particular cyclic or polycyclic structure containing two or three unsaturations, solid catalyst components and catalysts therefrom, the catalysts comprising the reaction product of:
i. a solid catalyst component containing an internal donor;
ii. an Al-alkyl compound, and optionally
iii. an external donor;
the internal donor and/or the external donor being cyclopolyenic 1,3-diethers. The catalysts are useful for the polymerization of alpha-olefins.

10 Claims, No Drawings

1,3-DIETHERS AND COMPONENTS AND CATALYSTS FOR THE POLYMERIZATION OF OLEFINS, CONTAINING SAID DIETHERS

This application is a division of application Ser. No. 08/603,497, filed Feb. 20, 1996 and now abandoned.

The present invention concerns catalysts for the polymerization of olefins, comprising particular 1,3-diethers.

Published European patent application n. 361 494 describes solid catalyst components comprising, as an internal electron-donor, an ether containing two or more ether groups, and having specific reaction characteristics toward the anhydrous magnesium chloride and $TiCl_4$.

The catalysts obtained from the reaction of said catalyst components with an Al-alkyl compound exhibit high activity and stereospecificity in the polymerization of olefins, and do not require the use of an external electron-donor.

It has now been found that by reacting an Al-alkyl compound with a solid catalyst component comprising magnesium dihalide in active form, a titanium compound and a 1,3-diether in which the carbon atom in position 2 belongs to a specific cyclic structure containing two or three unsaturations (cyclopolyenic structure), a catalyst is obtained which has uncommonly high catalytic activity and a high level of stereospecificity in the polymerization of olefins.

In fact, the above mentioned 1,3-diethers with a cyclopolyenic structure (hereinafter cyclopolyenic 1,3-diethers), which are not disclosed in published European patent application n. 361 494, confer to the above mentioned catalyst an activity considerably higher than the one obtained by using the ethers known in the art.

The addition of an external electron-donor to the above catalyst, containing the cyclopolyenic 1,3-diether as internal electron-donor, allows one to obtain very high levels of stereospecificity while maintaining high activity. Thus one obtains balances of activity and stereospecificity that cannot be reached with the ethers known in the art.

Published European patent application n. 362705 describes catalysts comprising the reaction product of a solid catalyst component comprising a titanium compound and an internal electron-donor supported on a magnesium dihalide in active form, an Al-alkyl compound, and, as an external electron-donor, an ether containing two or more ether groups and capable of forming complexes with anhydrous magnesium chloride, under standard conditions, in quantities lower than 60 mmoles per 100 g of magnesium chloride.

Said catalysts exhibit high activity and stereospecificity in the polymerization of olefins.

It has now been found that the performance of the above mentioned catalysts is improved when the previously said cyclopolyenic 1,3-diethers are used as the external electron-donors.

In fact, the catalysts obtained by using, as the external-electron donors, the above mentioned cyclopolyenic 1,3-diethers, which are not disclosed in published European patent application n. 362705, display, in the polymerization of olefins, very high balances of activity and stereospecificity not obtainable with the ethers known in the art.

Accordingly the present invention provides a solid catalyst component for the polymerization of olefins, said solid catalyst component comprising a magnesium halide in active form, and, supported thereon, a titanium compound containing at least one Ti-halogen bond and, as the internal electron-donor compound, a cyclopolyenic 1,3-diether in which the carbon atom in position 2 belongs to a cyclic or polycyclic structure made up of 5, 6, or 7 carbon atoms, or of 5-n or 6-n' carbon atoms, and respectively n nitrogen atoms and n' heteroatoms selected from the group consisting of N, O, S and Si, where n is 1 or 2 and n' is 1, 2, or 3, said structure containing two or three unsaturations (cyclopolyenic structure), and optionally being condensed with other cyclic structures, or substituted with one or more substituents selected from the group consisting of linear or branched alkyl radicals; cycloalkyl, aryl, aralkyl, alkaryl radicals and halogens, or being condensed with other cyclic structures and substituted with one or more of the above mentioned substituents that can also be bonded to the condensed cyclic structures; one or more of the above mentioned alkyl, cycloalkyl, aryl, aralkyl, or alkaryl radicals and the condensed cyclic structures optionally containing one or more heteroatoms as substitutes for carbon or hydrogen atoms, or both.

According to another embodiment, the present invention provides a catalyst for the polymerization of olefins comprising the reaction product of:
a) a catalyst component as defined above;
b) an Al-alkyl compound, and optionally
c) an electron-donor compound.

According to another embodiment, the present invention provides a catalyst for the polymerization of olefins comprising the reaction product of an Al-alkyl compound and a cyclopolyenic 1,3-diether with a solid catalyst component $a^1$) comprising a magnesium halide in active form, and, supported thereon, a titanium compound containing at least one Ti-halogen bond and an electron-donor compound.

The catalyst component a) is a preferred example of catalyst component $a^1$).

Preferably in the cyclopolyenic 1,3-diethers employed in preparing the catalyst component (a) the carbon atoms in positions 1 and 3 are secondary.

The above substituents in the cyclopolyenic 1,3-diethers are preferably selected from the group consisting of $C_1$–$C_{20}$ linear or branched alkyl radicals; $C_3$–$C_{20}$ cycloalkyl; $C_6$–$C_{20}$ aryl, $C_7$–$C_2$, aralkyl and $C_7$–$C_{20}$ alkaryl radicals; Cl and F.

The heteroatoms optionally present in the alkyl, cycloalkyl, aryl, aralkyl, alkaryl radicals and/or in the condensed cyclic structures are preferably selected from the group consisting of N; O; S; P; Si and halogens, in particular Cl and F.

Preferred among the above cyclopolyenic 1,3-diethers are the compounds of the general formula:

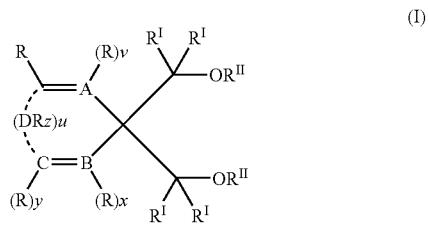

(I)

where A, B, C and D are carbon atoms or heteroatoms selected from the group consisting of N, O, S and Si; v, x and y are 0 or 1; u and z are 0 or 1 or 2;

provided that when u=0:

i) A, B and C are carbon atoms and v, x and y are equal to 1; or ii) A is a nitrogen atom, B and C are carbon atoms, v is equal to 0, and x and y are equal to 1; or iii) A and B are nitrogen atoms, C is a carbon atom, v and x are equal to 0, and y is equal to 1; or
iv) A and B are carbon atoms, C is a nitrogen atom, v and x are equal to 1, and y is equal to 0;

when u=1:
1) A, B, C and D are carbon atoms, v, x and y are equal to 1, and z is equal to 2; or
2) A and B are carbon atoms, C is a nitrogen atom, D is an oxygen atom, v and x are equal to 1, y and z are equal to 0; or
3) A, B and C are carbon atoms, D is an oxygen, nitrogen, sulfur, or silicon atom, v, x and y are equal to 1, and z is equal to 0 when D is an oxygen or sulfur atom, equal to 1 when D is a nitrogen atom, and equal to 2 when D is a silicon atom;

when u=2:
A, B and C are carbon atoms, D represents two carbon atoms bonded to each other by a single or double bond, v, x and y are equal to 1, and z is equal to 1 when the couple of carbon atoms D is bonded by a double bond, and equal to 2 when said couple is bonded by a single bond;

radicals R and $R^I$, equal or different, are selected from the group consisting of hydrogen; halogens, preferably Cl and F; $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals; the $R^{II}$ radicals, equal or different, are selected from the group consisting of $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals, and two or more of the R radicals can be bonded to each other to form condensed cyclic structures, saturated or unsaturated, optionally substituted with $R^{III}$ radicals selected from the group consisting of halogens, preferably Cl and F; $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals; said radicals from R to $R^{III}$ optionally containing one or more heteroatoms as substitutes for carbon or hydrogen atoms, or both.

Preferably, in the cyclopolyenic 1,3-diethers employed in preparing the catalyst component a) all the $R^I$ radicals in the compounds of formula (I) are hydrogen, and the two $R^{II}$ radicals are methyl.

The heteroatoms optionally present in the radicals from R to $R^{III}$ are preferably selected from the group consisting of N; O; S; P; Si and halogens, in particular Cl and F.

A more restricted class of the compounds of formula (I) is constituted by the compounds of the general formula:

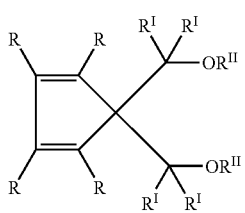

(II)

where the radicals from R to $R^{II}$ have the meaning defined above for formula (I), including the preferred cases.

In particular, two or more of the R radicals can be bonded to each other to form one or more condensed cyclic structures, preferably benzenic, optionally substituted by $R^{III}$ radicals.

Specially-preferred are the compounds of formula:

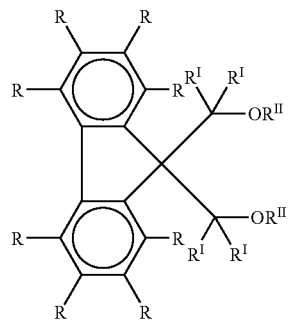

where the R radicals, equal or different, are hydrogen; halogens, preferably Cl and F; $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals, optionally containing one or more heteroatoms selected from the group consisting of N, O, S, P, Si and halogens, in particular Cl and F, as substitutes for carbon or hydrogen atoms, or both; the radicals $R^I$ and $R^{II}$ are as defined above for formula (I).

Specific examples of compounds comprised in formula (II) are:
1,1-bis(methoxymethyl)-cyclopentadiene;
1,1-bis(methoxymethyl)-2,3,4,5-tetramethylcyclopentadiene;
1,1-bis(methoxymethyl)-2,3,4,5-tetraphenylcyclopentadiene;
1,1-bis(methoxymethyl)-2,3,4,5-tetrafluorocyclopentadiene;
1,1-bis(methoxymethyl)-3,4-dicyclopentylcyclopentadiene;
1,1-bis(methoxymethyl)indene;
1,1-bis(methoxymethyl)-2,3-dimethylindene;
1,1-bis(methoxymethyl)-4,5,6,7-tetrahydroindene;
1,1-bis(methoxymethyl)-2,3,6,7-tetrafluoroindene;
1,1-bis(methoxymethyl)-4,7-dimethylindene;
1,1-bis(methoxymethyl)-3,6-dimethylindene;
1,1-bis(methoxymethyl)-4-phenylindene;
1,1-bis(methoxymethyl)-4-phenyl-2-methylindene;
1,1-bis(methoxymethyl)-4-cyclohexylindene;
1,1-bis(methoxymethyl)-7-(3,3,3-trifluoropropyl)indene;
1,1-bis(methoxymethyl)-7-trimethylsilylindene;
1,1-bis(methoxymethyl)-7-trifluoromethylindene;
1,1-bis(methoxymethyl)-4,7-dimethyl-4,5,6,7-tetrahydroindene;
1,1-bis(methoxymethyl)-7-methylindene;
1,1-bis(methoxymethyl)-7-cyclopenthylindene;
1,1-bis(methoxymethyl)-7-isopropylindene;
1,1-bis(methoxymethyl)-7-cyclohexylindene;
1,1-bis(methoxymethyl)-7-tert-butylindene;
1,1-bis(methoxymethyl)-7-tert-butyl-2-methylindene;
1,1-bis(methoxymethyl)-7-phenylindene;
1,1-bis(methoxymethyl)-2-phenylindene;
1,1-bis(methoxymethyl)-1H-benz[e]indene;
1,1-bis(methoxymethyl)-1H-2-methylbenz[e]indene;
9,9-bis(methoxymethyl)fluorene;
9,9-bis(methoxymethyl)-2,3,6,7-tetramethylfluorene;
9,9-bis(methoxymethyl)-2,3,4,5,6,7-hexafluorofluorene;
9,9-bis(methoxymethyl)-2,3-benzofluorene;
9,9-bis(methoxymethyl)-2,3,6,7-dibenzofluorene;
9,9-bis(methoxymethyl)-2,7-diisopropylfluorene;
9,9-bis(methoxymethyl)-1,8-dichlorofluorene;
9,9-bis(methoxymethyl)-2,7-dicyclopentylfluorene;

9,9-bis(methoxymethyl)-1,8-difluorofluorene;
9,9-bis(methoxymethyl)-1,2,3,4-tetrahydrofluorene;
9,9-bis(methoxymethyl)-1,2,3,4,5,6,7,8-octahydrofluorene;
9,9-bis(methoxymethyl)-4-tert-butylfluorene.

Other examples of cyclopolyenic 1,3-diethers comprised in the definitions above are:
1,1-bis(1'-butoxyethyl)-cyclopentadiene;
1,1-bis(1'-isopropoxy-n.propyl)cyclopentadiene;
1-methoxymethyl-1-(1'-methoxyethyl)-2,3,4,5-tetramethylcyclopentadiene;
1,1-bis(α-metoxybenzyl)indene;
1,1-bis(phenoxymethyl)indene;
1,1-bis(1'-methoxyethyl)-5,6-dichloroindene;
1,1-bis(phenoxymethyl)-3,6-dicyclohexylindene;
1-methoxymethyl-1-(1'-methoxyethyl)-7-tert-butylindene;
1,1-bis[2-(2'methoxypropyl)]-2-methylindene;
3,3-bis(methoxymethyl)-3H-2-methylbenz[e]indene;
9,9-bis(α-methoxybenzyl)fluorene;
9,9-bis(1'-isopropoxy-n.butyl)-4,5-diphenylfluorene;
9,9-bis(1'-methoxyethyl)fluorene;
9-(methoxymethyl)-9-(1'-methoxyethyl)-2, 3, 6, 7-tetrafluorofluorene;
9-methoxymethyl-9-pentoxymethylfluorene;
9-methoxymethyl-9-ethoxymethylfluorene;
9-methoxymethyl-9-(1'methoxyethyl)-fluorene;
9-methoxymethyl-9-[2-(2-methoxypropyl)]-fluorene;
1,1-bis(methoxymethyl)-2,5-cyclohexadiene;
1,7-bis(methoxymethyl)benzonaphthene;
7,7-bis (methoxymethyl)2,5-norbornadiene;
9,9-bis(methoxymethyl)-1,4-methanedihydronaphthalene;
4,4-bis(methoxymethyl)-4H cyclopenta[d,e,f]phenanthrene;
9,9-bis(methoxymethyl)9,10-dihydroanthracene;
7,7-bis(methoxymethyl)-7H-benz[d,e]anthracene;
1,1-bis(methoxymethyl)1,2-dihydronaphthalene;
4,4-bis(methoxymethyl)-1-phenyl-3,4-dihydronaphthalene;
4,4-bis(methoxymethyl)-1-phenyl-1,4-dihydronaphthalene;
5,5-bis(methoxymethyl)-1,3,6-cycloheptatriene;
5,5-bis(methoxymethyl)-10,11-dihydro-5H-dibenzo[a,d]cycloheptene;
5,5-bis(methoxymethyl)-5H-dibenzo[a,d]cycloheptene;
9,9-bis(methoxymethyl)xanthene;
9,9-bis(methoxymethyl)-2,3,6,7-tetramethylxanthene;
9,9-bis(1'methoxyisobutyl)thioxanthene;
4,4-bis(methoxymethyl)-1,4-pyran;
9,9-bis(methoxymethyl)-N-tert-butyl-9,10-dihydroacridine;
4,4-bis(methoxymethyl)-1,4-chromene;
4,4-bis(methoxymethyl)-1,2,4-oxazine;
1,1-bis(methoxymethyl)benzo-2,3,1-oxazine;
5,5-bis(methoxymethyl)-1,5-pyrindine;
5,5-bis(methoxymethyl)-6,7-dimethyl-1,5-pyrindine;
2,2-bis(methoxymethyl)-3,4,5-trifluoroisopyrrole;
4,4-bis(1'methoxyethyl)benzo-N-phenyl-1,4-dihydropyridine.

The cyclopolyenic 1,3-diethers of the present invention can be synthesized by various reactions. One of them consists of causing to react, in the presence of a base, a compound of the following general formula:

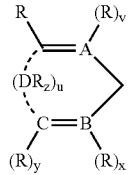

where u, v, x, y, z, A, B, C, D, and the R radicals are as defined for general formula (I), with compounds of the formula $XC(R^I)_2$—$OR^{II}$, where X represents Cl, Br, and I, and $R^I$ and $R^{II}$ are as defined for general formula (I). However, this way of synthesizing has the inconvenience of producing low yields.

The diethers of the present invention can also be synthesized from the corresponding diols by an etherification reaction as described, for example, in European patent applications EP-A-361493 and EP-A-487035. The etherification reaction described in these applications requires that a diol, or the corresponding alkaline alcoholate, in a suitable organic solvent is reacted with an $R^{II}X$ compound, or a $(R^{II})_2SO_4$ compound, where $R^{II}$ is as defined for general formula (I), and X is Cl, Br, I, $CH_3SO_3$, $C_6H_5$—$SO_3$, or p-$CH_3$—$C_6H_4$—$SO_3$, in the presence of a base. According to the examples of said applications the etherification reaction is carried out by mixing the diol, or corresponding alkaline alcoholate, with the base in an organic solvent, and then adding the $R^{II}X$ or $(R^{II})_2SO_4$ compound. Optionally base and $R^{II}X$ or $(R^{II})_2SO_4$ compound can added subsequently.

This reaction produces yields that do not exceed 80%, and in same cases requires long synthesis periods.

Now a synthesis process has been found that allows to obtain the diethers of the present invention with higher etherification yields. Also, less reaction time is needed for the etherification reaction. Said process can be used for the synthesis of the propane-1,3-diethers described in the above mentioned European patent application EP-A-361493.

Another object of the present invention is the process for the synthesis of diethers of general formula (III)

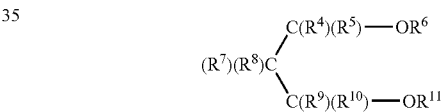

where the $R^7$ and $R^8$ radicals, equal or different, are hydrogen or $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals; the $R^4$, $R^5$, $R^9$, and $R^{10}$ radicals, equal or different, have the same meaning as defined for the $R^7$ and $R^8$ radicals; the $R^6$ and $R^{11}$ radicals have the same meaning as the $R^7$ and $R^8$ radicals except for the hydrogen; moreover, two or more radicals from $R^4$ to $R^{10}$ can be bonded to form a cyclic structure; said radicals from $R^4$ to $R^{11}$ optionally containing one or more heteroatoms, as substitutes for one or more carbon or hydrogen atoms, or both, selected from N, O, S, P, Si and halogens, preferably Cl and F.

Said process comprises the following steps:
a) mixing a diol of general formula (IV)

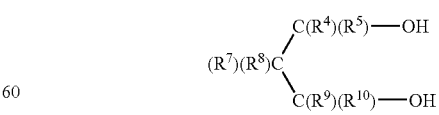

where the radicals from $R^4$ to $R^{10}$ are as defined for general formula (III), with a compound or mixture of compounds selected from the compounds of general formulae $R^6X$ (V), or general formula $R^{11}X$ (VI), where X is Cl, Br, I, $CH_3SO_3$, $C_6H_5$—$SO_3$, or p-$CH_3$—$C_6H_4$—

$SO_3$, or of general formula $(R^6)_2SO_n$ (VII), or of general formula $(R^{11})_2SO_n$ (VIII), where $R^6$ and $R^{11}$ have the meaning as defined for general formula (III), and n is 3 or 4, in a solvent which is basically nonreactive toward the reagents; and then b) adding a base which is substantially inert towards the compounds of general formulae (V) to (VIII), and is capable of forming the alcoholated derivative of the corresponding diol (IV) under the reaction conditions.

Preferably, the above mentioned bases are selected from the bases of alkaline metals. Examples of bases that can be used in the process of the present invention are sodium hydride and sodium hydroxide. In the specific case where sodium hydroxide is used, the preferred solvent is the dimethyl sulfoxide.

Preferably the base is added gradually. For example it is possible to introduce the base in a period of time ranging from 10 minutes to 4 hours.

Examples of solvents suitable for use in the process of the present invention include tetrahydrofuran, dimethyl sulfoxide, diethyl ether, aliphatic hydrocarbons, such as pentane, heptane, hexane, or aromatic hydrocarbons such as toluene and benzene, and dimethylformamide.

Specific reaction conditions, such as temperature and pressure, are not crucial for the reaction to occur; for example the temperature can range from 0° to 100° C., and the operation can take place at ambient pressure.

It is preferable to carry out the above mentioned reaction by using quantities of the compound or mixture of compounds of formulae (V) to (VIII) in excess with respect to the diol (IV). In particular, the molar ratio of the diol to the compound or mixture of compounds (V)–(VIII) is preferably comprised from 1:3 to 1:15.

Examples of synthesis of diols of formula (IV) are already known in literature; for example synthesis processes are disclosed in above cited European patent applications EP-A-361493 and EP-A-487035.

The diols corresponding to the diethers of formula (I) can be prepared according to various known synthesis processes, for example, by aldol condensation of the corresponding unsaturated cyclic compounds, such as fluorene, indene, cyclopentadiene, with proper aldehydes (see Acta Chemica Scandinavica 21, 1967, pp. 718–720, for example).

Examples of specific diols corresponding to the diethers of formula (I) and their related synthesis disclosed in literature, are 9,9-bis(hydroxymethyl)fluorene (see Acta Chemica Scandinavica 21, 1967, pp. 718–720), 9-hydroxymethyl-9-(α-nethyl)hydroxymethylfluorene (see Chemical Abstract, CAS number: 101168-93-8), 9-(α-methyl)hydroxymethyl-9-(α'-methyl)hydroxymethylfluorene (see Beilstein, registration number: 101594-61-0), and 9-(α-phenyl)hydroxymethyl-9-(α'-phenyl)hydroxymethylfluorene (see Beilstein, registration number: 103210-68-0).

The electron-donor compound present in the solid catalyst component $a^1$) can be a Lewis base containing one or more electronegative groups where the electron-donor atoms are selected from the group consisting of N, O, S, P, As or Sn. Examples of the above mentioned electron-donor compounds are widely described in the art. Preferred are the electron-donor compounds that can be extracted with Al-triethyl from the catalyst component $a^1$) for at least 70% in moles, the surface area (B.E.T.) of the solid product of extraction being at least 20 $m^2/g$, and generally ranging from 100 to 300 $m^2/g$.

Examples of the above mentioned electron-donor compounds are described in U.S. Pat. No. 4,522,930, and comprise ethers, ketones, lactones, compounds containing N, P, and/or S atoms, and specific types of esters.

In addition to the esters of U.S. Pat. No. 4,522,930, the esters described in European patent n. 045977 can be used.

Particularly suited are the phthalic acid esters such as diisobutyl, dioctyl and diphenyl phthalate, benzyl-butyl phthalate; the malonic acid esters such as diisobutyl and diethyl malonate; the alkyl and aryl pivalates; the alkyl, cycloalkyl, and aryl maleates; the alkyl and aryl carbonates such as diisobutyl carbonate, ethyl-phenyl carbonate and diphenyl carbonate; the succinic acid esters such as mono and diethyl succinate. Preferred are the phthalic acid esters.

Also useful in the catalyst component $a^1$) are the electron-donor compounds described in published European patent application n. 361494.

Said compounds are ethers that contain two or more ether groups, and that, under standard conditions, are capable of forming complexes with anhydrous magnesium chloride for less that 60 mmoles per 100 g of chloride and with $TiCl_4$ they do not undergo substitution reactions, or they only do so for less than 50% in moles.

The tests that allow the verification of the above reactivity criteria are reported below.

Complexing Test of the Ethers with $MgCl_2$

In a 100 ml glass flask with fixed blades mechanical stirrer are introduced under nitrogen atmosphere in order:

70 ml of anhydrous n-heptane 12 mmoles of anhydrous $MgCl_2$ activated as described below 2 mmoles of ether.

The content is allowed to react at 60° C. for 4 hours (stirring speed at 400 rpm). It is then filtered and washed at ambient temperature with 100 ml of n-heptane after which it is dried with a mechanical pump.

The solid is characterized, after having been treated with 100 ml of ethanol, by way of a gas chromatographic quantitative analysis for the analysis of the quantity of ether fixed.

Test of the Reaction with $TiCl_4$.

In a 25 ml test-tube with a magnetic stirrer and under nitrogen atmosphere are introduced:

10 ml of anhydrous n-heptane 5 mmoles of $TiCl_4$ 1 mmole of donor

The content is allowed to react at 70° C. for 30 minutes, after which it is cooled to 25° C. and decomposed with 90 ml of ethanol.

The solutions obtained are analyzed by way of gas chromatography using the internal standard method, with an HRGC 5300 Mega Series Carlo Erba gas chromatograph with a 25 meters chrompack CP-SIL 5CB capillary column.

The magnesium chloride used in the complexing test with the ethers is prepared as follows.

In a 1 liter vibrating mill jar (Vibratom from Siebtechnik) containing 1.8 Kg of steel spheres 16 mm in diameter, are introduced under nitrogen atmosphere 50 g of anhydrous $MgCl_2$ and 6.8 ml of 1,2-dichloroethane (DCE).

The content is milled at room temperature for 96 hours, after which the solid recovered is kept under vacuum in the mechanical pump for 16 hours at 50° C.

Characterization of the solid:

half-peak breadth of the reflection D110=1.15 cm.

Presence of a halo with maximum intensity at $2\theta=32.1°$

Surface area (B.E.T.)=125 $m^2/g$ residual DCE=2.5% by weight.

Examples of ethers having the features indicated above are the 1,3-diethers of formula

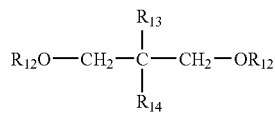

where $R_{12}$, $R_{13}$ and $R_{14}$ are the same or different and are linear or branched $C_1$–$C_{18}$ alkyl, $C_3$–$C_{18}$ cycloalkyl, $C_6$–$C_{18}$ aryl, $C_7$–$C_{18}$ aralkyl or alkaryl radicals, and $R_{13}$ or $R_{14}$ can also be a hydrogen atom.

Preferably, $R_{12}$ is a 1–6 carbon alkyl radical, and more particularly a methyl. Moreover, when $R_{13}$ is methyl, ethyl, propyl, or isopropyl, $R_{14}$ can be ethyl, propyl, isopropyl, butyl, isobutyl, tert-butyl, 2-ethylhexyl, cyclopenthyl, cyclohexyl, methylcyclohexyl, phenyl or benzyl; when $R_{13}$ is hydrogen, $R_{14}$ can be ethyl, butyl, sec.butyl, tert-butyl, 2-ethylhexyl, cyclohexylethyl, diphenylmethyl, p-chlorophenyl, 1-naphthyl, 1-decahydronaphthyl; $R_{13}$ and $R_{14}$ can also be the same and can be ethyl, propyl, isopropyl, butyl, isobutyl, tert-butyl, neopentyl, phenyl, benzyl, cyclohexyl, cyclopentyl.

Specific examples of ethers that can be advantageously used include: 2-(2-ethylhexyl)1,3-dimethoxypropane, 2-isopropyl-1,3-dimethoxypropane, 2-butyl-1,3-dimethoxypropane, 2-sec-butyl-1,3-dimethoxypropane, 2-cyclohexyl-1,3-dimethoxypropane, 2-phenyl-1,3-dimethoxypropane, 2-tert-butyl-1,3-dimethoxypropane, 2-cumyl-1,3-dimethoxypropane, 2-(2-phenylethyl)-1,3-dimethoxypropane, 2-(2-cyclohexylethyl)-1,3-dimethoxypropane, 2-(p-chlorophenyl)-1,3-dimethoxypropane, 2-(diphenylmethyl)-1,3-dimethoxypropane, 2(1-naphthyl)-1,3-dimethoxypropane, 2(p-fluorophenyl)-1,3-dimethoxypropane, 2(1-decahydronaphthyl)-1,3-dimethoxypropane, 2(p-tert-butylphenyl)-1,3-dimethoxypropane, 2,2-dicyclohexyl-1,3-dimethoxypropane, 2,2-diethyl-1,3-dimethoxypropane, 2,2-dipropyl-1,3-dimethoxypropane, 2,2-dibutyl-1,3-dimethoxypropane, 2,2-diethyl-1,3-diethoxypropane, 2,2-dicyclopentyl-1,3-dimethoxypropane, 2,2-dipropyl-1,3-diethoxypropane, 2,2-dibutyl-1,3-diethoxypropane, 2-methyl-2-ethyl-1,3-dimethoxypropane, 2-methyl-2-propyl-1,3-dimethoxypropane, 2-methyl-2-benzyl-1,3-dimethoxypropane, 2-methyl-2-phenyl-1,3-dimethoxypropane, 2-methyl-2-cyclohexyl-1,3-dimethoxypropane, 2-methyl-2-methylcyclohexyl-1,3-dimethoxypropane, 2,2-bis(p-chlorophenyl)-1,3-dimethoxypropane, 2,2-bis(2-phenylethyl)-1,3-dimethoxypropane, 2,2-bis(2-cyclohexylethyl)-1,3-dimethoxypropane, 2-methyl-2-isobutyl-1,3-dimethoxypropane, 2-methyl-2-(2-ethylhexyl)-1,3-dimethoxypropane, 2,2-bis(2-ethylhexyl)-1,3-dimethoxypropane,2,2-bis (p-methylphenyl)-1,3-dimethoxypropane, 2-methyl-2-isopropyl-1,3-dimethoxypropane, 2,2-diisobutyl-1,3-dimethoxypropane, 2,2-diphenyl-1,3-dimethoxypropane, 2,2-dibenzyl-1,3-dimethoxypropane, 2 -isopropyl-2-cyclopentyl-1,3-dimethoxypropane, 2,2-bis(cyclohexylmethyl)-1,3-dimethoxypropane, 2,2-diisobutyl-1,3-diethoxypropane, 2,2-diisobutyl-1,3-dibuthoxypropane, 2-isobutyl-2-isopropyl-1,3-dimetoxypropane, 2,2-di-sec-butyl-1,3-dimetoxypropane, 2,2-di-tert-butyl-1,3-dimetoxypropane, 2,2-dineopentyl-1,3-dimetoxypropane, 2-isopropyl-2-isopentyl-1,3-dimetoxypropane, 2-phenyl-2-benzyl-1,3-dimetoxypropane, 2-cyclohexyl-2-cyclohexylmethyl-1,3-dimethoxypropane.

The preparation of the solid catalyst components a) and $a^1$) can be carried out using various methods.

For example, the magnesium halide (used anhydrous, containing less than 1 of water), the titanium compound, and the electron-donor compound are milled together under conditions that cause the activation of the magnesium halide; the milled product is then caused to react one or more times with $TiCl_4$ in excess, optionally in the presence of an electron-donor, at a temperature ranging from 80 to 135° C., and then repeatedly washed with a hydrocarbon (such as hexane, for example) until no chlorine ions can be detected in the wash liquid.

According to another method the anhydrous magnesium halide is preactivated according to known methods and then reacted with an excess of $TiCl_4$ containing the electron-donor compound and optionally an aliphatic, cycloaliphatic, aromatic or chlorinated hydrocarbon solvent (for example: hexane, heptane, cyclohexane, toluene, ethylbenzene, chlorobenzene, dichloroethane). In this case also the operation takes place at a temperature between 80° and 135° C. The reaction with $TiCl_4$, in the presence or absence of an electron-donor, is optionally repeated and the solid is then washed with hexane to eliminate the nonreacted $TiCl_4$.

According to another method, a $MgCl_2.nROH$ adduct (particularly in the form of spheroidal particles) where n is generally from 1 to 3, and ROH is an alcohol, such as ethanol, butanol, isobutanol for example, is caused to react with an excess of $TiCl_4$ containing the electron-donor compound and optionally one of the above mentioned hydrocarbon solvents. The reaction temperature initially is from 0 to 25° C., and is then increased to 80–135° C. After reaction, the solid is reacted once more with $TiCl_4$, in the presence or absence of the electron-donor, then separated and washed with a hydrocarbon until no chlorine ions can be detected in the wash liquid.

According to yet another method, magnesium alcoholates and chloroalcoholates (the chloroalcoholates can be prepared particularly as described in U.S. Pat No. 4,220,554) are caused to react with $TiCl_4$ in excess containing the electron-donor compound, operating under the reaction conditions already described.

According to another method, complexes of magnesium halides with titanium alcoholates (the $MgCl_2.2Ti(OC_4H_9)_4$ complex is a typical example) are caused to react, in a hydrocarbon solution, with $TiCl_4$ in excess containing the electron-donor compound; the separated solid product is reacted again with an excess of $TiCl_4$, in the presence or absence of electron-donor, and then separated and washed with hexane. The reaction with $TiCl_4$ is carried out at a temperature ranging from 80° to 130° C.

According to a variance, the $MgCl_2$ and titanium alcoholate complex is caused to react in a hydrocarbon solution with polyhydrosiloxane; the separated solid product is reacted at 50° C. with silicon tetrachloride containing the electron-donor compound; the solid is then reacted with $TiCl_4$ in excess, in the presence or absence of electron-donor, operating at 80°–130° C.

Independently from the specific preparation method, after the last reaction with $TiCl_4$ in the presence of the electron-donor, it is preferable to separate the solid obtained (by way of filtration, for example), and cause it to react with an excess of $TiCl_4$ at temperatures ranging from 80 to 135° C., before washing it with the hydrocarbon solvent.

Finally, it is possible to cause to react $TiCl_4$ in excess and containing the electron-donor with porous resins such as partially cross-linked styrene-divinylbenzene in spherical particle form, or porous inorganic oxides such as silica and alumina, impregnated with solutions of magnesium compounds or complexes soluble in organic solvents.

The porous resins which can be used are described in published European patent application 344755.

The reaction with $TiCl_4$ is carried out at 80–100° C. After separating the excess $TiCl_4$, the reaction is repeated and the solid is then washed with a hydrocarbon.

The $MgCl_2$/electron-donor molar ratio used in the reactions indicated above generally ranges from 4:1 to 12:1.

The electron-donor compound is fixed on the magnesium halide in a quantity generally ranging from 1 to 20% molar.

In particular, the cyclopolyenic 1,3-diether is fixed on the magnesium halide in a quantity generally ranging from 5 to 20% molar.

In the solid catalyst components a) and $a^1$) the Mg/Ti ratio is generally from 30:1 to 4:1; in the components supported on resins or on inorganic oxides the ratio can be different and usually ranges from 20:1 to 2:1.

The titanium compounds that can be used for the preparation of catalyst components a) and $a^1$) are the halides and halogen alcoholates. The titanium tetrachloride is the preferred compound. Satisfactory results can also be obtained with the trihalides, particularly $TiCl_3$ HR, $TiCl_3$ ARA, and with the halogen alcoholates such as $TiCl_3$ OR, where R is a phenyl radical, for example.

The above reactions cause the formation of magnesium halide in active form. In addition to these reactions, other reactions are known in the literature that bring to the formation of magnesium halide in active form starting from magnesium compounds different from the halides.

The active form of the magnesium halides present in the catalyst components of the invention is recognizable by the fact that in the X-rays spectrum of the catalyst component the major intensity reflection which appears in the spectrum of the nonactivated magnesium halides (having surface area smaller than 3 m$^2$/g) is no longer present, but in its place there is a halo with the position of the maximum intensity shifted with respect to the position of the major intensity reflection, or by the fact that the major intensity reflection presents a half-peak breadth at least 30% greater that the one of the corresponding reflection of the nonactivated Mg halide. The most active forms are those in which the halo appears in the X-ray spectrum of the solid catalyst component.

Among the magnesium halides, the chloride is the preferred compound. In the case of the most active forms of the magnesium chloride, the halo appears in place of the reflection which in the spectrum of the nonactivated magnesium chloride is situated at the interplanar distance of 2.56 Å.

The catalyst components a) and $a^1$) form, by reaction with the Al-alkyl compounds, catalysts which can be used in the polymerization of $CH_2$=CHR olefins, where R is hydrogen or a 1–6 carbon alkyl radical, or an aryl radical, or mixtures of said olefins or of said olefins and diolefins.

However the present invention requires the use of an external electron-donor with the catalyst, component $a^1$), at least when the latter is different from the catalyst component a).

The Al-alkyl compounds comprise Al-trialkyls such as Al-triethyl, Al-triisobutyl, Al-tri-n-butyl, Al-trioctyl. One can also use linear or cyclic Al-alkyl compounds containing one or more Al atoms bonded to one another with O, N, or S atoms.

Examples of said compounds are:

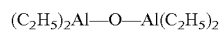

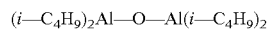

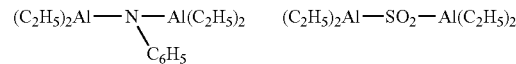

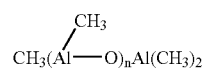 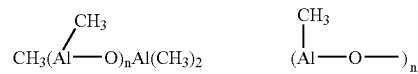

where n is a number from 1 to 20; $AlR_2OR'$ compounds where R' is a $C_6$–$C_{20}$ aryl radical substituted at position 2 and/or 6, and R is a $C_1$–$C_6$ alkyl radical, and $AlR_2H$ compounds where R is a $C_1$–$C_6$ alkyl radical.

The Al-Alkyl compound is used in Al/Ti ratios generally ranging from 1 to 1000.

The trialkyl compounds can also be used in blends with Al-alkyl halides such as $AlEt_2Cl$ and $AlEt_{3/2}Cl_{3/2}$.

The polymerization of the olefins is carried out according to known methods operating in liquid phase constituted by one or more monomers, or by a solution of one or more monomers in an aliphatic or aromatic hydrocarbon solvent, or in gas phase, or also by combining polymerization stages in liquid phase and in gas phase.

The (co)polymerization temperature is usually from 0° to 150° C.; particularly from 60° to 100° C. The operation occurs at atmospheric pressure or higher.

The catalysts can be precontacted with small quantities of olefins (prepolymerization). The prepolymerization improves the performance of the catalysts as well as the morphology of the polymers.

The prepolymerization is carried out maintaining the catalysts in suspension in a hydrocarbon solvent (hexane or heptane, for example), adding an olefin, and operating at temperatures ranging from room temperature to 60° C. producing a quantity of polymer generally from 0.5 to 3 times the weight of the catalyst. It can also be carried out in liquid monomer, under the temperature conditions indicated above, and producing quantities of polymer which can reach 1000 g per g of catalytic component.

When the catalyst component a) is to be employed in the stereoregular polymerization of olefins, propylene in particular, an external electron-donor can be added to the Al-alkyl, said external electron-donor compound being preferably selected from the group consisting of silicon compounds containing at least one Si—OR bond (R=hydrocarbon radical); 2,2,6,6-tetramethylpiperidine; 2,6-diisopropylpiperidine; carboxylic acid esters, such as ethylparatoluate and ethylbenzoate, and di- and polyethers.

Preferably the silicon compounds have the formula $R^{15}{}_nSi(OR^{16})_{4-n}$ where n is 1 or 2, the $R^{15}$ radical or radicals, same or different, are $C_1$–$C_{12}$ alkyl, $C_3$–$C_{12}$ cycloalkyl, $C_6$–$C_{12}$ aryl, $C_7$–$C_{12}$ alkaryl or aralkyl radicals,

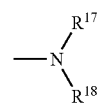

radicals, where $R^{17}$ and $R^{18}$ are the same or different and have the same meaning defined above for $R^{15}$, or are bonded to each other to form a cyclic structure; the $R^{16}$ radicals are the same or different and are $C_1$–$C_6$ alkyl radicals.

Optionally the $R^{15}$ to $R^{18}$ radicals can contain one or more halogens, in particular Cl and F, as substitutes for hydrogen atoms.

Examples of said compounds are:
(tert-butyl)$_3$Si(OCH$_3$)$_2$;
(cyclohexyl)$_2$Si(OCH$_3$)$_2$;
(isopropyl)$_2$Si(OCH$_3$)$_2$;
(sec-butyl)$_2$Si(OCH$_3$)$_2$;
(cyclohexyl)(methyl)Si(OCH$_3$)$_2$;
(cyclopentyl)$_2$Si(OCH$_3$)$_2$;
(isopropyl)(methyl)Si(OCH$_3$)$_2$;
(n-butyl)$_2$Si(OCH$_3$)$_2$;
(isobutyl)$_2$Si(OCH$_3$)$_2$;
(sec-butyl)$_2$Si(OCH$_3$)$_2$;
(tert-butyl)(methyl)Si(OCH$_3$)$_2$;
(tert-amyl)(methyl)Si(OCH$_3$)$_2$;
(tert-hexyl)(methyl)Si(OCH$_3$)$_2$;
(2-norbornyl)(methyl)Si(OCH$_3$)$_2$;
(tert-butyl)(cyclopentyl)Si(OCH$_3$)$_2$;
(2-norbornyl)(cyclopentyl)Si(OCH$_3$)$_2$;
(tert-butyl)Si(OCH$_3$)$_3$;
(tert-butyl)Si(OC$_2$H$_5$)$_3$;
(2-norbornyl)Si(OCH$_3$)$_3$;
(2-norbornyl)Si(OC$_2$H$_5$)$_3$;
(tert-hexyl)Si(OCH$_3$)$_3$;
(tert-hexyl)Si(OC$_2$H$_5$)$_3$;
(tert-butyl)(2-methylpiperidyl)Si(OCH$_3$)$_2$;
(tert-butyl)(3-methylpiperidyl)Si(OCH$_3$)$_2$;
(tert-butyl)(4-methylpiperidyl)Si(OCH$_3$)$_2$;
(tert-hexyl)(piperidyl)Si(OCH$_3$)$_2$;
(tert-hexyl)(pyrrolidinyl)Si(OCH$_3$)$_2$;
(methyl)(3,3,3-trifluoropropyl)Si(OCH$_3$)$_2$;
(isopropyl)(3,3,3-trifluoropropyl)Si(OCH$_3$)$_2$;
(n-butyl)(3,3,3-trifluoropropyl)Si(OCH$_3$)$_2$;
(isobutyl)(3,3,3-trifluoropropyl)Si(OCH$_3$)$_2$;
(sec-butyl)(3,3,3-trifluoropropyl)Si(OCH$_3$)$_2$;
(tert-butyl)(3,3,3-trifluoropropyl)Si(OCH$_3$)$_2$;
(3,3,3-trifluoropropyl)(piperidyl)Si(OCH$_3$)$_2$;
(3,3,3-trifluoropropyl)(2-methylpiperidyl)Si(OCH$_3$)$_2$;
(3,3,3-trifluoropropyl)(2-ethylpiperidyl)Si(OCH$_3$)$_2$;
(3,3,3-trifluoropropyl)(3-methylpiperidyl)Si(OCH$_3$)$_2$;
(3,3,3-trifluoropropyl)(4-methylpiperidyl)Si(OCH$_3$)$_2$;
(3,3,3-trifluoropropyl)$_2$Si(OCH$_3$)$_2$.

Examples of preferred diethers that can be used as external electron-donors with the catalyst component a) are the compounds of the general formula

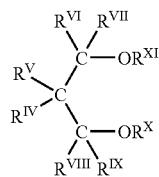

where $R^{IV}$, $R^V$, $R^{VI}$, $R^{VII}$, $R^{VIII}$ and $R^{IX}$ are the same or different, and are hydrogen; linear or branched $C_1$–$C_{18}$ alkyl radicals, $C_3$–$C_{18}$ cycloalkyl, $C_6$–$C_{18}$ aryl, $C_7$–$C_{18}$ aralkyl or alkaryl radicals, provided that only one of $R^{IV}$ and $R^V$ can be hydrogen; $R^X$ and $R^{XI}$ have the same meaning as $R^{IV}$ and $R^V$ except for hydrogen, provided that when the radicals from $R^V$ to $R^{IX}$ are hydrogen and $R^X$ and $R^{XI}$ are methyl, $R^{XV}$ is not methyl; moreover, two or more of the $R^{VI}$ to $R^{XI}$ radicals can be bonded to form a cyclic structure.

Preferably in the above formula $R^X$ and $R^{XI}$ are methyl and $R^{IV}$ and $R^V$ are the same or different and are selected from the group consisting of isopropyl; isobutyl; tert-butyl; cyclohexyl; isopentyl; cyclohexylethyl; pentyl; cyclopentyl; heptyl; 1,5-dimethylhexyl; 3,7-dimethyloctyl; phenyl; cyclohexylmethyl; and propyl.

Specific examples of the above mentioned diethers are: 2,2-diisobutyl-1,3-dimethoxypropane; 2-isopropyl-2-isopentyl-1,3-dimethoxypropane; 2,2-diisopropyl-1,3-dimethoxypropane; 2-isopropyl-2-cyclohexylmethyl-1,3-dimethoxypropane; 2,2-diphenyl-1,3-dimethoxypropane.

Additional examples of diethers having the above mentioned formula are listed in published European patent application n. 362 705.

Particularly preferred for use as external electron-donors with the catalyst component a) are the cyclopolyenic 1,3-diethers.

The molar ratio of the Al-alkyl compound to the external electron-donor generally is from 5:1 to 100:1, and preferably from 10:1 to 30:1; said ratio can be broader, for example from 0.5:1 to 100:1, during the prepolymerization phase.

The catalysts find particular application in the polymerization of $CH_2$=CHR olefins where R is a 1–6 carbon alkyl or aryl radical. In particular, said catalysts are adequate for the polymerization of propylene or its copolymerization with ethylene or other α-olefins.

Carrying out the polymerization in liquid monomer operating with Al/Ti ratios lower than 50, it is possible to obtain, thanks to the high productivity of the catalysts of the present invention, hyperpure homopolymers and copolymers of propylene useful in the electronic field (capacitor grade).

The catalysts of the present invention are also adequate for the production of polyethylenes and copolymers of ethylene with α-olefins, such as 1-butene, 1-hexene, and 1-octene.

The following examples are given in order to illustrate and not limit the invention.

Unless otherwise indicated, the percentages in the examples are expressed by weight.

The melt flow rate (MFR) for polypropylene is determined according to ASTM D1238, condition L.

The intrinsic viscosity [η] is determined in tetrahydronaphthalene at 135° C.

In order to determine the fraction insoluble in xylene at 25° C. (X.I. %), 2.5 g of polymer are dissolved under agitation in 250 ml of xylene at 135° C., and after 20 minutes it is allowed to cool to 25° C. After 30 minutes the precipitated polymer is filtered and dried at reduced pressure at 80° C. until constant weight is reached.

Synthesis of 9.9-bis(hydroxymethyl)fluorene

In a 500 ml flask, in anhydrous atmosphere, are introduced in order: 100 ml of dimethyl sulfoxide (DMSO) distilled on CaH, 8 g of paraformaldehyde (rendered anhydrous at ambient temperature and at a pressure of 2 torr for 8 hours), and 1.4 g of sodium ethylate dissolved in 6 ml of ethanol.

After having cooled the suspension with an ice bath (the melt temperature of the DMSO/EtOH mixture is 13° C.), while maintaining the suspension under agitation, 100 ml of a solution of 16 g of fluorene in DMSO are added, in a period of thirty seconds.

After 3 minutes from the beginning of the addition of the solution of fluorene in DMSO, the reaction is stopped with 1.5 ml of HCl at 37%, and then it is diluted with 400 ml of water.

The mixture is saturated with NaCl, and the 9,9-bis(hydroxymethyl)fluorene is extracted with ethyl acetate. The organic phase is then rendered anhydrous with anhydrous $Na_2SO_4$ and the solvent is distilled off. After crystallization by way of toluene, 15.2 g of product (yield: 70%) is obtained.

The $^1$H-NMR spectrum in $CDCl_3$, at 200 MHz and using tetramethylsilane (TMS) as internal standard, shows the following:

| | | |
|---|---|---|
| 7.77 ppm, | doublet, | 2H aromatics |
| 7.62 ppm, | doublet, | 2H aromatics |
| 7.41 ppm, | triplet, | 2H aromatics |
| 7.32 ppm | triplet, | 2H aromatics |
| 3.99 ppm | doublet, | 4H $CH_2$ |
| 0.25 ppm, | triplet, | 2H OH. |

EXAMPLE 1

Synthesis of 9,9-bis(methoxymethyl)fluorene

In a 100 ml flask are introduced, in nitrogen atmosphere, in order: 30 ml of tetrahydrofuran (THF), 11.3 g of 9,9-bis(hydroxymethyl)fluorene, and 31.1 ml of $CH_3I$.

While maintaining under agitation and operating at ambient temperature, 4 g of NaH at 60% by weight in mineral oil is added, in a period of 2 hours and 30 minutes, and the content is then allowed to react for 1 hour and 30 minutes.

By way of distillation the nonreacted $CH_3I$ is recovered, and the remaining content is diluted with 100 ml of water; the resulting floating solid is filtered and dried under vacuum at 40° C. By way of ethanol crystallization, 11.3 g of product (yield: 90%) is obtained.

The $^1$H-NMR spectrum in $CDCl_3$, at 200 MHz and using TMS as internal standard, shows the following:

| | | |
|---|---|---|
| 7.75 ppm, | doublet, | 2H aromatics |
| 7.65 ppm, | doublet, | 2H aromatics |
| 7.39 ppm, | triplet, | 2H aromatics |
| 7.29 ppm | triplet, | 2H aromatics |
| 3.64 ppm | singlet, | 4H $CH_2$ |
| 3.35 ppm, | singlet, | 6H $CH_3$. |

EXAMPLE 2

In a 500 ml cylindrical glass reactor equipped with a filtering barrier are introduced at 0° C. 225 ml of $TiCl_4$, and, while under agitation in a period of 15 minutes, 10.1 g (54 mmoles) of microspheroidal $MgCl_2.2.1\ C_2H_5OH$ obtained as described below.

At the end of the addition, the temperature is brought to 70° C., and 9 mmoles of 9,9-bis(methoxymethyl)fluorene are introduced. The temperature is increased to 100° C. and, after 2 hours, the $TiCl_4$ is removed by filtration. 200 ml of $TiCl_4$ and 9 mmoles of 9,9-bis(methoxymethyl)fluorene are added; after 1 hour at 120° C. the content is filtered again and another 200 ml of $TiCl_4$ are added, continuing the treatment at 120° C. for one more hour; finally, the content is filtered and washed at 60° C. with n-heptane until all chlorine ions disappear from the filtrate. The catalyst component obtained in this manner contains: Ti=3.5% by weight; 9,9-bis(methoxymethyl)fluorene=16.2% by weight.

The microspheroidal $MgCl_2.2.1\ C_2H_5OH$ is prepared as follows.

48 g of anhydrous $MgCl_2$, 77 g of anhydrous $C_2H_5OH$, and 830 ml of kerosene are fed, in inert gas and at ambient temperature, in a 2 liter autoclave equipped with a turbine agitator and drawing pipe. The content is heated to 120° C. while stirring thus forming the adduct between $MgCl_2$ and the alcohol that melts and remains mixed with the dispersing agent. The nitrogen pressure inside the autoclave is maintained at 15 atm. The drawing pipe of the autoclave is heated externally to 120° C. with a heating jacket, has an inside diameter of 1 mm, and is 3 meters long from one end of the heating jacket to the other.

Then the mixture is caused to flow through the pipe at a velocity of 7 m/sec ca.

At the exit of the pipe the dispersion is gathered in a 5 l flask, under agitation, containing 2.5 l of kerosene, and being externally cooled by way of a jacket maintained at an initial temperature of −40° C.

The final temperature of the dispersion is 0° C.

The spherical solid product that constituted the dispersed phase of the emulsion is separated by way of settling and filtration, and then washed with heptane and dried.

All these operations are carried out in an inert gas atmosphere.

130 g of $MgCl_2.3\ C_2H_5OH$ in the form of spherical solid particles with a maximum diameter less than or equal to 50 micron, are obtained.

The alcohol is removed from the product thus obtained at temperatures that gradually increase from 50° C. to 100° C. in nitrogen current until the alcohol content is reduced to 2.1 moles per mole of $MgCl_2$.

In a 4 liter autoclave, previously purged with gaseous propylene at 70° C. for 1 hour, are introduced at ambient temperature and in propylene current 70 ml of anhydrous n-hexane containing 7 mmoles of aluminum triethyl and 4 mg of the solid catalyst component prepared as described above. The autoclave is closed, 1.7 Nl of hydrogen and 1.2 kg of liquid propylene are introduced; the agitator is put in motion and the temperature is increased to 70° C. in a period of 5 minutes. After 2 hours at 70° C., the agitation is interrupted, the nonpolymerized monomer is removed, and the content is cooled to ambient temperature.

380 g of polypropylene is discharged from the autoclave, said polypropylene having a fraction insoluble in xylene at 25° C. (X.I.)=97.7%, and a melt index MFR/L=4.5 g/10 min. The polymer yield is 95,000 g of polypropylene/g of solid catalyst component.

EXAMPLE 3

The procedure of Example 2 is used, except that the hexane suspension introduced in the polymerization autoclave is made up as follows: 70 ml of anhydrous n-hexane, 7 mmoles of aluminum triethyl, 5.3 mg of a solid catalyst component prepared as described in Example 2, and 0.35 mmoles of dicyclopentyl-dimethoxysilane. 403 g of polypropylene having X.I.=99% and melt index MFR/L=4.2 g/10 min. is obtained. The polymer yield is 76,000 g of polypropylene/g of solid catalyst component.

COMPARATIVE EXAMPLE 1

The procedure of Example 2 is used, but in this case in order to prepare the solid catalyst component, two aliquots equal to 9 mmoles each of 2-isopropyl-2-isopentyl-1,3-dimethoxypropane are used instead of 9,9-bis(methoxymethyl)fluorene. The solid catalyst component thus obtained contains: Ti=3.6% by weight; 2-isopropyl-2-isopentyl-1,3-dimethoxypropane=12.7% by weight.

The polymerization is then conducted as described in Example 2, using 5.7 mg of the above mentioned solid catalyst component. 400 g of polypropylene having X.I.=98.0% and melt index MFR/L=5.1 g/10 min. is obtained. The polymer yield is 70,000 g of polypropylene/g of solid catalyst component.

COMPARATIVE EXAMPLE 2

The procedure of Example 3 is used, but in this case the hexane suspension introduced in the polymerization autoclave is made up as follows: 70 ml of anhydrous n-hexane, 7 mmoles of aluminum triethyl, 7.0 mg of solid catalyst component prepared as described in Comparative Example 1, and 0.35 mmoles of dicyclopentyldimethoxysilane. 350 g of polypropylene having X.I.=98.9% and melt index MFR/L=5.5 g/10 min. is obtained.

The polymer yield is 50,000 g of polypropylene/g of solid catalyst component.

EXAMPLE 4

In the autoclave described in Example 2, previously purged with gaseous propylene at 70° C. for 1 hour, are introduced at ambient temperature in order: 4.1 g of ethylene, 1.2 l of liquid propylene, and 0.34 l of hydrogen. The agitator is put in motion, the temperature is increased to 70° C. in a period of 5 minutes, and by way of a steel syringe pressurized with nitrogen, a suspension composed of 10 ml of anhydrous n-hexane, 4 mmoles of aluminum triethyl, and 4 mg of a solid catalyst component prepared as described in Example 2 is introduced.

The stirring is maintained for 1.5 hours at 70° C. and 32.7 bar, while feeding a propylene/ethylene mixture containing 5.9% moles of ethylene. At the end, the stirring is interrupted, the nonpolymerized monomers are removed, and the content is cooled to ambient temperature. 600 g of copolymer having an ethylene content of 4% by weight, X.I.=91.6%, and an intrinsic viscosity [η]=1.59 dl/g is obtained. The copolymer yield is 150,000 g of propylene-ethylene copolymer/g of solid catalyst component.

COMPARATIVE EXAMPLE 3

Example 4 is repeated, but using in this case 4.1 mg of the solid catalyst component prepared according to comparative Example 1 (containing 2-isopropyl-2-isopentyl-1,3-dimethoxypropane instead of 9,9-bis(methoxymethyl)fluorene). One obtains 420 g of copolymer having an ethylene content of 3.9% by weight, X.I.=90.7%, and intrinsic viscosity [η]=1.55 dl/g is obtained. The copolymer yield is 102,000 g of propylene-ethylene copolymer/g of solid catalyst component.

EXAMPLE 5

Example 3 is repeated using 5.2 mg of the solid catalyst component of Example 2, but in this case the hexane suspension of the catalyst contains 0.35 mmoles of 2-isopropyl-2-isopentyl-1,3-dimethoxypropane instead of 0.35 mmoles of dicyclopentyldimethoxysilane. 314 g of polypropylene having X.I.=99.0% is obtained. The polymer yield is 60,000 g of polypropylene/g of catalyst component.

COMPARATIVE EXAMPLE 4

Example 2 is repeated, but in this case to prepare the solid catalyst component, two aliquots equal to 9 mmoles each of 2,2-diisobutyl-1,3-dimethoxypropane are used instead of 9,9-bis(methoxymethyl)fluorene. The product obtained comprises: Ti=2.8% by weight; 2,2-diisobutyl-1,3-dimethoxypropane=14.7% by weight. Using 6.1 mg of solid catalyst component, 260 g of polypropylene having X.I.=96.9% and melt index MFR/L=4.9 g/10 min. is obtained. The polymer yield is 42,600 g of polypropylene/g of catalyst component.

COMPARATIVE EXAMPLE 5

Example 2 is repeated, but in this case the solid catalyst component is prepared by using two aliquots equal to 9 mmoles each of 2,2-diisopentyl-1,3-dimethoxypropane instead of 9,9-bis(methoxymethyl)fluorene. The product contains: Ti=2.6% by weight; 2,2-diisopentyl-1,3-dimethoxypropane=17.6% by weight. By using 7.3 mg of solid catalyst component, 332 g of polypropylene having X.I.=95.2% and a melt index MFR/L=5.2 g 10 min. is obtained.

The polymer yield is 45,400 g of polypropylene/g of catalyst component.

COMPARATIVE EXAMPLE 6

Example 2 is repeated, but in this case the solid catalyst component is prepared by using two aliquots equal to 9 mmoles each of 2-isopropyl-2-cyclohexyl-1,3-dimethoxypropane instead of 9,9-bis(methoxymethyl)fluorene. The product obtained contains: Ti=3.2% by weight; 2-isopropyl-2-cyclohexyl-1,3-dimethoxypropane=13.2% by weight. By using 6.5 mg of solid catalyst component, 261 g of polypropylene having X.I.=97.2% and melt index MFR/L=5.9 g 10/min. is obtained.

The yield is 40,200 g of polypropylene/g catalyst component.

EXAMPLE 6

In a 500 ml cylindrical glass reactor equipped with a filtering barrier are introduced at 0° C. 225 ml of TiCl$_4$ and, while under agitation in a period of 15 minutes, 10.1 g (54 mmoles) of microspheroidal MgCl$_2$.2.1 C$_2$H$_5$OH obtained as described in Example 2.

At the end of the addition, the temperature is brought to 40° C. and 9 mmoles of diisobutyl phthalate are introduced.

The temperature is increased to 100° C. in the course of 1 hour, and the stirring continues for an additional 2 hours. The TiCl$_4$ is then removed by filtration, 200 ml of TiCl$_4$ are added while continuing the stirring at 120° C. for one more hour. Finally, the content is filtered and washed at 60° C. with n-heptane until all chlorine ions disappear from the filtrate. The catalyst component obtained in this manner contains: Ti=3.3% by weight; diisobutyl phthalate=8.2% by weight.

In a 4 liter autoclave, previously purged with gaseous propylene at 70° C. for 1 hour, are introduced at ambient temperature and in propylene current 70 ml of anhydrous n-hexane containing 7 mmoles of aluminum triethyl and 0.35 mmoles of 9,9-bis(methoxymethyl)fluorene, and 10 mg of the solid catalyst component prepared as described above. The autoclave is closed, 1.7 Nl of hydrogen and 1.2 kg of liquid propylene are introduced; the agitator is put in motion and the temperature is increased to 70° C. in a period of 5 minutes. After 2 hours at 70° C., the agitation is interrupted, the nonpolymerized monomer is removed, and the content is cooled to ambient temperature.

450 g of polypropylene is discharged from the autoclave, said polypropylene having a fraction insoluble in xylene at 25° C. (X.I.)=97.5% and a melt index MFR/L=5.0 g/10 min. The polymer yield is 45,000 g of polypropylene/g of solid catalyst component.

COMPARATIVE EXAMPLE 7

Example 6 is repeated using 8.9 mg of the solid catalyst component of Example 6, but in this case 0.35 mmoles of 2-isopropyl,2-isopentyl-1,3-dimethoxypropane are used as the external electron-donor compound with the aluminum triethyl (instead of the 9,9-bis(methoxymethyl)fluorene). 339 g of polypropylene are obtained, said polypropylene having X.I.=97.7% and melt index MFR/L=5.2 g/10 min. The polymer yield is 38,000 g of polypropylene/g of solid catalyst component.

EXAMPLE 7

In a 500 ml cylindrical glass reactor equipped with a filtering barrier are introduced at 0° C. 225 ml of $TiCl_4$ and, while under agitation in a period of 15 minutes, 10.1 g (54 mmoles) of microspheroidal $MgCl_2.2.1$ $C_2H_5OH$ obtained as described in Example 2.

At the end of the addition, the, temperature is brought to 70° C. and 9 mmoles of 2-isopropyl-2-isopentyl-1,3-dimethoxypropane are introduced.

The temperature is increased to 100° C. and after 2 hours the $TiCl_4$ is removed by filtration. An additional 200 ml of $TiCl_4$ and 9 mmoles of 2-isopropyl-2-isopentyl-1,3-dimethoxypropane are added; after one hour at 120° C. the content is filtered again and another 200 ml of $TiCl_4$ are added proceeding with the treatment at 120° C. for another hour; finally the content is filtered and washed at 60° C. with n-heptane until all chlorine ions disappear from the filtrate. The solid catalyst component obtained in this manner contains: Ti=3.6% by weight; 2-isobutyl-2-isopentyl-1,3-dimethoxypropane=12.7% by weight.

Carrying out the polymerization as described in Example 6, and using 9.7 mg of the catalyst component described above, 484 g of polymer having X.I.=99% and melt index MFR/L=5.1 g/10 min. is obtained.

The polymer yield is 50,000 g of polypropylene/g of solid catalyst component.

EXAMPLE 8

Example 7 is repeated, but using in this case 5.3 mg of the solid catalyst component of Example 2.

371 g of polypropylene having X.I.=99.1% and MFR/L=5.1 g/10 min. is obtained.

The polymer yield is 70,000 g of polypropylene/g of catalyst component.

COMPARATIVE EXAMPLE 8

Comparative Example 7 is repeated, but in this case 0.35 mmoles of 2,2-diisobutyl-1,3-dimethoxypropane is used as the external electron-donor compound with the aluminum triethyl.

Using 9.5 mg of solid catalyst component, 290 g of polypropylene having X.I.=97.0% and melt index MFR/L=5.6 g/10 min. is obtained. The yield is 30,500 g of polypropylene/g of catalyst component.

COMPARATIVE EXAMPLE 9

Comparative Example 7 is repeated, but in this case 0.35 mmoles of 2-isopropyl-2-isobutyl-1,3-dimethoxypropane is used as the external electron-donor compound with the aluminum triethyl.

Using 10 mg of solid catalyst component, 353 g of polypropylene having X.I.=97.2% and melt index MFR/L=4.6 g/10 min. is obtained. The yield is 35,300 g of polypropylene/g of catalyst component.

COMPARATIVE EXAMPLE 10

Comparative Example 7 is repeated, but in this case 0.35 mmoles of 2,2-diisopropyl-1,3-dimethoxypropane is used as the external electron-donor compound with the aluminum triethyl. Using 10.2 mg of solid catalyst component, 403 g of polypropylene having X.I.=98% and melt index MFR/L=5.1 g/10 min. is obtained. The yield is 39,500 g of polypropylene/g of catalyst component.

COMPARATIVE EXAMPLE 11

Comparative Example 7 is repeated, but in this case 0.35 mmoles of 2-ethyl-2-butyl-1,3-dimethoxypropane is used as the external electron-donor compound with the aluminum triethyl. Using 9.8 mg of solid catalyst component, 307 g of polypropylene having X.I.=95.2% and melt index MFR/L=5.1 g/10 min. is obtained. The yield is 31,300 g of polypropylene/g of catalyst component.

COMPARATIVE EXAMPLE 12

Comparative Example 7 is repeated, but in this case 0.35 mmoles of 2,2-diphenyl-1,3-dimethoxypropane is used as the external electron-donor compound with the aluminum triethyl. Using 8.7 mg of solid catalyst component, 347 g of polypropylene having X.I.=98.0% and melt index MFR/L=3.1 g/10 min. is obtained. The yield is 40,000 g of polypropylene/g of catalyst component.

COMPARATIVE EXAMPLE 13

Comparative Example 7 is repeated, but in this case 0.35 mmoles of 2-isopropyl-2-cyclohexyl-1,3-dimethoxypropane is used as the external electron-donor compound with the aluminum triethyl.

Using 9.1 mg of solid catalyst component, 297 g of polypropylene having X.I.=98.0% and melt index MFR/L=3.8 g/10 min. is obtained. The yield is 32,600 g of polypropylene/g of catalyst component.

COMPARATIVE EXAMPLE 14

Comparative Example 7 is repeated, but in this case 0.35 mmoles of 2,2-dicyclopentyl-1,3-dimethoxypropane is used as the external electron-donor compound with the aluminum triethyl. Using 9.6 mg of solid catalyst component, 385 g of polypropylene having X.I.=97.9% and melt index MFR/L=3.2 g/10 min. is used. The yield is 40,100 g of polypropylene/g of catalyst component.

COMPARATIVE EXAMPLE 15

Synthesis of 9,9-bis(methoxymethyl)fluorene

Into a 250 mL flask are introduced 36 ml of a 50% aqueous solution of NaOH, 84 ml of toluene, 9.6 g of 9,9-bis(hydroxymethyl)fluorene, and 0.24 g of tetrabutylammonium hydrogen sulfate.

After heating the resulting mixture to 40° C., 8 ml of $CH_3I$ are added dropwise over a period of 1 hour; at the end of the addition the content is allowed to react for 4 hours at 40° C.

It is then cooled to ambient temperature, diluted with 40 ml of water, and the organic phase is then separated. The aqueous phase is extracted with toluene, then the toluene extracts put together are rendered anhydrous with anhydrous $Na_2SO_4$ and the solvent is flashed off. After an ethanol crystallization 3 g of product (yield: 28%) is obtained.

COMPARATIVE EXAMPLE 16

Synthesis of 9,9-bis(methoxymethyl)fluorene

Into a 250 ml flask are introduced, in anhydrous atmosphere, 100 ml of THF and 10 g of 9,9-bis(hydroxymethyl) fluorene. Then at ambient temperature 1.8 g of NaH at 60% by weight in mineral oil is added portionwise over a period of 30 minutes, and immediately thereafter 2.3 ml of $CH_3I$ are added dropwise over a period of 30 minutes. The solution is allowed to react for 3 hours.

A second addition is then made consisting of 1.8 g of NaH and 2.3 ml of $CH_3I$ in the same manner described above. After 3 hours of reaction time the content is diluted with 300 ml of water and then the floating solid is separated and crystallized. 5.6 g of product (yield: 50%) is obtained. Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

The invention claimed is:

1. A diether having the general formula:

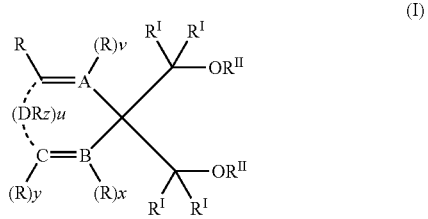

(I)

where A, B, C and D are carbon atoms or heteroatoms selected from the group consisting of N, O, S and Si; v, x and y are 0 or 1; u and z are 0 or 1 or 2;

provided that when u=0:
  i) A, B and C are carbon atoms and v, x and y are equal to 1; or
  ii) A is a nitrogen atom, B and C are carbon atoms, v is equal to 0 and x and y are equal to 1; or
  iii) A and B are nitrogen atoms, C is a carbon atom, v and x are equal to 0 and y is equal to 1; or
  iv) A and B are carbon atoms, C is a nitrogen atom, v and x are equal to 1 and y is equal to 0;

when u=1:
  1) A, B, C and D are carbon atoms, v, x and y are equal to 1 and z is equal to 2; or
  2) A and B are carbon atoms, C is a nitrogen atom, D is an oxygen atom, v and x are equal to 1, y and z are equal to 0; or
  3) A, B and C are carbon atoms, D is an oxygen, nitrogen, sulfur, or silicon atom, v, x and y are equal to 1 and z is equal to 0 when D is an oxygen or sulfur atom, equal to 1 when D is a nitrogen atom, and equal to 2 when D is a silicon atom;

when u=2:
A, B and C are carbon atoms, D represents two carbon atoms bonded to each other by a single or double bond, v, x and y are equal to 1 and z is equal to 1 when the couple of carbon atoms D is bonded by a double bond, and equal to 2 when said couple is bonded by a single bond; radicals R and $R^I$, equal or different, are selected from the group consisting of hydrogen; halogens; $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals; the $R^{II}$ radicals, equal or different, are selected from the group consisting of $C_1$–$C_{20}$ radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals, and two or more of the R radicals can be bonded to each other to form condensed cyclic structures, saturated or unsaturated, optionally substituted with $R^{III}$ radicals selected from the group consisting of halogens; $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals; said radicals from R to $R^{III}$ optionally containing one or more heteroatoms as substitutes for carbon or hydrogen atoms, or both.

2. The diether of claim 1, wherein the heteroatoms optionally present in the radicals from R to $R^{III}$ are selected from the group consisting of N, S, O, P, Si, Cl, and F.

3. The diether of claim 1, having formula (II)

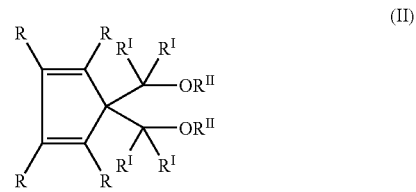

(II)

where the radicals from R to $R^{II}$ are as defined for formula (I).

4. The diether of claim 3, where two or more R radicals are bonded to each other to form one or more condensed cyclic structures, optionally substituted by $R^{III}$ radicals.

5. The diether of claim 3, where the condensed cyclic structures are benzenic structures, optionally substituted by $R^{III}$ radicals.

6. The diether of claim 3 selected from the group consisting of:
1,1-bis(methoxymethyl)-cyclopentadiene;
1,1-bis(methoxymethyl)-2,3,4,5-tetramethylcyclopentadiene;
1,1-bis(methoxymethyl)-2,3,4,5-tetraphenylcyclopentadiene;
1,1-bis(methoxymethyl)indene;
1,1-bis(methoxymethyl)-2,3-dimethylindene;
1,1-bis(methoxymethyl)-4,7-dimethylindene;
1,1-bis(methoxymethyl)-4-phenyl-2-methylindene;
1,1-bis(methoxymethyl)-7-(3,3,3-trifluoropropyl)indene;
1,1-bis(methoxymethyl)-7-trimethylsilylindene;
1,1-bis(methoxymethyl)-7-trifluoromethylindene;
1,1-bis(methoxymethyl)-7-methylindene;
1,1-bis(methoxymethyl-7-cyclopentylindene;
1,1-bis(methoxymethyl)-7-isopropylindene;
1,1-bis(methoxymethyl)-7-cyclohexylindene;
1,1-bis(methoxymethyl)-7-tert-butylindene;
1,1-bis(methoxymethyl)-7-tert-butyl-2-methylindene;
1,1-bis(methoxymethyl)-7-phenylindene;
1,1-bis(methoxymethyl)-2-phenylindene;
9,9-bis(methoxymethyl)-fluorene;
9,9-bis(methoxymethyl)-2,3,6,7-tetramethylfluorene;
9,9-bis(methoxymethyl)-2,3,4,5,6,7-hexafluorofluorene;
9,9-bis(methoxymethyl)-2,3-benzofluorene;
9,9-bis(methoxymethyl)-2,3,6,7-dibenzofluorene;
9,9-bis(methoxymethyl)-2,7-diisopropylfluorene;
9,9-bis(methoxymethyl)-1,8-dichlorofluorene;
9,9-bis(methoxymethyl)-2,7-dicyclopentylfluorene;
9,9-bis(methoxymethyl)-1,8-difluorofluorene;
9,9-bis(methoxymethyl)-1,2,3,4-tetrahydrofluorene;
9,9-bis(methoxymethyl)-1,2,3,4,5,6,7,8-octahydrofluorene;
9,9-bis(methoxymethyl)-4-tert-butylfluorene;
1,1-bis(α-methoxybenzyl)indene;
1,1-bis(1'-methoxyethyl)-5,6-dichloroindene;
9,9-bis(α-methoxybenzyl)fluorene;
9,9-bis(1'-methoxyethyl)fluorene;
9-methoxymethyl-9-(1'-methoxyethyl)-2,3,6,7-tetrafluorofluorene;
9-methoxymethyl-9-pentoxymethylfluorene;
9-methoxymethyl-9-ethoxymethylfluorene;
9-methoxymethyl-9-(1'methoxyethyl)-fluorene; and
9-methoxymethyl-9-[2-(2-methoxypropyl)]-fluorene.

7. The diether of claim 1 selected from the group consisting of:
1,1-bis(methoxymethyl)benzonaphthene;
9,9-bis(methoxymethyl)-9,10-dihydroanthracene;
9,9-bis(methoxymethyl)xanthene; and
9,9-bis(methoxymethyl)-2,3,6,7-tetramethylxanthene.

8. A process for the synthesis of diethers of formula (I)

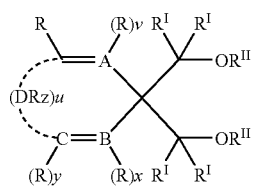

(I)

where A, B, C and D are carbon atoms or heteroatoms selected from the group consisting of N, O, S and Si; v, x and y are 0 or 1; u and z are 0 or 1 or 2;

provided that when u=0:
i) A, B and C are carbon atoms and v, x and y are equal to 1; or
ii) A is a nitrogen atom, B and C are carbon atoms, v is equal to 0 and x and y are equal to 1; or
iii) A and B are nitrogen atoms, C is a carbon atom, v and x are equal to 0 and y is equal to 1; or
iv) A and B are carbon atoms, C is a nitrogen atom, v and x are equal to 1 and y is equal to 0;

when u=1:
1) A, B, C and D are carbon atoms, v, x and y are equal to 1 and z is equal to 2; or
2) A and B are carbon atoms, C is a nitrogen atom, D is an oxygen atom, v and x are equal to 1, y and z are equal to 0; or
3) A, B and C are carbon atoms, D is an oxygen, nitrogen, sulfur, or silicon atom, v, x and y are equal to 1 and z is equal to 0 when D is an oxygen or sulfur atom, equal to 1 when D is a nitrogen atom, and equal to 2 when D is a silicon atom;

when u=2:
A, B and C are carbon atoms, D represents two carbon atoms bonded to each other by a single or double bond, v, x and y are equal to 1 and z is equal to 1 when the couple of carbon atoms D is bonded by a double bond, and equal to 2 when said couple is bonded by a single bond; radicals R and $R^I$, equal or different, are selected from the group consisting of hydrogen; halogens; $C_1$–$C_{20}$ alkyl radicals, linear or branched; $C_3$–$C_{20}$ cycloalkyl, $C_6$–$C_{2C}$ aryl, $C_7$–$C_{20}$ alkaryl and $C_7$–$C_{20}$ aralkyl radicals; the $R^{II}$ radicals, equal or different, are selected from the group consisting of $C_1$–$C_{20}$ radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals, and two or more of the R radicals can be bonded to each other to form condensed cyclic structures, saturated or unsaturated, optionally substituted with $R^{III}$ radicals selected from the group consisting of halogens; $C_1$–$C_{20}$ alkyl radicals, linear or branched; $C_3$–$C_{20}$ cycloalkyl, $C_6$–$C_{20}$ aryl, $C_7$–$C_{20}$ alkaryl and $C_7$–$C_{20}$ aralkyl radicals; said radicals from R to $R^{III}$ optionally containing one or more heteroatoms as substitutes for carbon or hydrogen atoms, or both, said process comprising:

a) mixing a diol of general formula (IX)

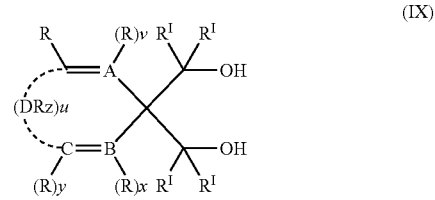

(IX)

where A, B, C and D, v, x, y, u and z, and the radicals R and $R^I$ are as defined for general formula (I), with a compound or a mixture of compounds selected from the compounds of general formulae $R^6X$ (V), or general formula $R^{11}X$ (VI), where X is Cl, a mixture of compounds selected from the compounds of general formulae $R^6X$ (V), or general formula $R^{11}X$ (VI), where X is Cl, Br, I, $CH_3SO_3$, $C_6H_5$—$SO_3$, or p-$CH_3$—$C_6H_4$—$SO_3$, or of general formula $(R^6)_2SO_n$ (VII), or of general formula $(R_{11})_2SO_n$ (VIII), wherein $R^6$ and $R^{11}$, equal or different, are selected from the group consisting of $C_1$–$C_{20}$ alkyl radicals, linear or branched;

$C_3$–$C_{20}$ cycloalkyl, $C_6$–$C_{20}$ aryl, $C_7$–$C_{20}$ alkaryl and $C_7$–$C_{20}$ aralkyl radicals; and n is 3 or 4, in a solvent which is basically nonreactive toward the reagents; and then b) adding a base which is substantially inert towards the compounds of general formula (V) to (VIII), and is capable of forming the alcoholated derivative of the corresponding diol (IX) under the reaction conditions.

9. The process of claim 8 where the base is sodium hydride or sodium hydroxide.

10. The process of claim 8, where the solvent is selected from the group consisting of tetrahydrofuran, dimethyl sulfoxide, diethyl ether, aliphatic or aromatic hydrocarbons, and dimethylformamide.

* * * * *